United States Patent
Sato et al.

Patent Number: 5,705,586
Date of Patent: Jan. 6, 1998

[54] ORGANIC FLUORINE COMPOUNDS AND CURABLE COMPOSITIONS

[75] Inventors: Shinichi Sato; Noriyuki Koike; Takashi Matsuda; Hirofumi Kishita; Masatoshi Arai, all of Gunma-ken, Japan

[73] Assignee: Shin-Etsu Chemical Co., Ltd., Tokyo, Japan

[21] Appl. No.: 494,566

[22] Filed: Jun. 22, 1995

[30] Foreign Application Priority Data

Jun. 23, 1994 [JP] Japan .................. 6-164635
Jun. 23, 1994 [JP] Japan .................. 6-164636
Nov. 4, 1994 [JP] Japan .................. 6-295789
Nov. 4, 1994 [JP] Japan .................. 6-295790

[51] Int. Cl.⁶ .................................. C08G 77/26
[52] U.S. Cl. .................. 528/15; 528/26; 528/28; 528/31; 528/32; 528/42; 556/419; 525/431
[58] Field of Search ............. 528/15, 31, 42, 528/28, 26; 556/419

[56] References Cited

U.S. PATENT DOCUMENTS

| | | | |
|---|---|---|---|
| 5,208,312 | 5/1993 | Boutevin et al. | 528/28 |
| 5,300,613 | 4/1994 | Kishita et al. | 528/26 |
| 5,352,752 | 10/1994 | Koike et al. | 528/26 |
| 5,380,811 | 1/1995 | Kishita et al. | 528/15 |
| 5,416,183 | 5/1995 | Sato | 528/15 |

*Primary Examiner*—Ralph H. Dean
*Attorney, Agent, or Firm*—Millen, White, Zelano & Branigan, PC

[57] ABSTRACT

Novel organic fluorine compounds are of formula (1):

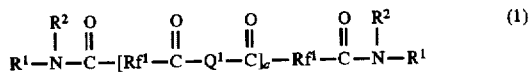

wherein $R^1$ and $R^2$ are monovalent hydrocarbon groups, $Q^1$ is a group of formula (2) or (3):

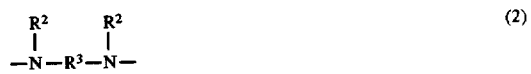

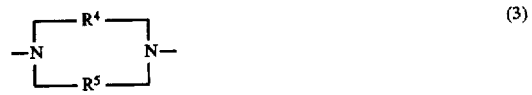

wherein $R^3$ is a divalent hydrocarbon group which may have an intervening oxygen, nitrogen or silicon atom, $R^4$ and $R^5$ are divalent hydrocarbon groups, $Rf^1$ is a divalent perfluoroalkylene or perfluoropolyether group, and letter a is an integer of 0–10. A curable composition comprising (A) a fluorinated amide compound having at least two aliphatic unsaturated groups of formula (1), (B) a fluorinated organohydrogensiloxane containing at least one monovalent perfluoroalkyl ether or perfluoroalkyl group and at least two hydrosilyl groups, and (C) a platinum group compound cures into elastomers solvent and chemical resistance.

18 Claims, 3 Drawing Sheets

5,705,586

ORGANIC FLUORINE COMPOUNDS AND CURABLE COMPOSITIONS

FIELD OF THE INVENTION

This invention relates to novel organic fluorine compounds which are useful as stock materials for rubber materials having solvent and chemical resistance and release agents. It also relates to curable compositions which when allowed to stand at room temperature or heated, will readily cure into cured products having improved solvent, chemical and heat resistance.

BACKGROUND OF THE INVENTION

Organic fluorine compounds have been used in a variety of fields. For example, polymers of organic fluorine compounds are crosslinked with crosslinking agents to form elastomers which are utilized as rubber materials and mold release agents. Most elastomers obtained from conventional organic fluorine compounds, however, are less resistant to solvents and chemicals. There is a need for elastomers having higher solvent and chemical resistance.

Elastomers used as sealants and molded parts are desired to exhibit better mold release and water repellent properties.

SUMMARY OF THE INVENTION

An object of the present invention is to provide a novel and improved organic fluorine compound which will form an elastomer having improved solvent resistance, chemical resistance, mold release properties, and water repellency.

Another object of the present invention is to provide a curable composition based on a fluorinated amide compound and a fluorinated organohydrogensiloxane which will cure into a cured product having improved solvent resistance, chemical resistance, mold release properties, and water repellency.

A first embodiment of the present invention provides an organic fluorine compound or fluorinated amide compound of the following general formula (1).

$$\overset{R^2}{\underset{R^1-N-C}{\mid}}\overset{O}{\underset{\parallel}{-}}[Rf^1-\overset{O}{\underset{\parallel}{C}}-Q^1-\overset{O}{\underset{\parallel}{C}}]_a-Rf^1-\overset{O}{\underset{\parallel}{C}}-\overset{R^2}{\underset{N-R^1}{\mid}} \quad (1)$$

In the formula, $R^1$ and $R^2$ are independently selected from substituted or unsubstituted monovalent hydrocarbon groups. $Q^1$ is a group represented by the following general formula (2) or (3):

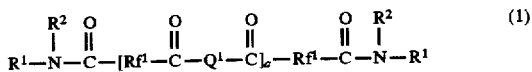

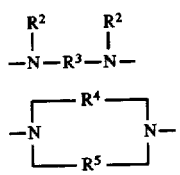

wherein $R^3$ is a substituted or unsubstituted divalent hydrocarbon group which may have at least one intervening atom selected from oxygen, nitrogen and silicon atoms, $R^4$ and $R^5$ are independently selected from substituted or unsubstituted divalent hydrocarbon groups. $Rf^1$ is a divalent perfluoroalkylene or perfluoropolyether group. Letter a is an integer inclusive of 0.

This novel organic fluorine compound of formula (1) can be obtained by reacting a compound having an acid fluoride group at either end of the following general formula (7) with a secondary amine compound of the following general formula (8) and optionally a compound of the following general formula (9) in the presence of an acid acceptor.

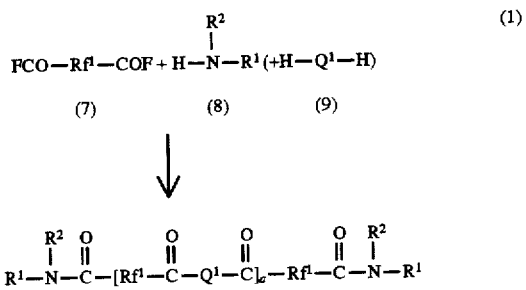

We have found that this organic fluorine compound can be converted into an elastomer having a higher fluorine content and lower surface energy.

A second embodiment of the present invention provides a curable composition comprising (A) a fluorinated amide compound having at least two aliphatic unsaturated groups in a molecule and represented by formula (1) as defined above, (B) a fluorinated organohydrogensiloxane containing at least one monovalent perfluoroalkyl ether or perfluoroalkyl group and at least two hydrosilyl groups in a molecule, and (C) a catalytic amount of a platinum group compound. Component (B) is present in an amount to give 0.5 to 5 mol of the hydrosilyl group per mol of the aliphatic unsaturated group in the composition.

A third embodiment of the present invention provides a curable composition comprising (D) a fluorinated amide compound having at least two aliphatic unsaturated groups in a molecule and represented by the following general formula (4):

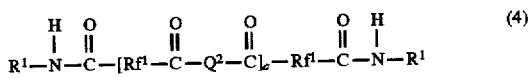

wherein $R^1$, $Rf^1$ and a are as defined above, $Q^2$ is a group of the following general formula (5):

wherein $R^3$ is as defined above, (E) a fluorinated organohydrogensiloxane containing in a molecule at least two hydrosilyl groups and at least one group of the following general formula (6):

wherein $Rf^2$ is a monovalent perfluoroalkyl or perfluoroalkyl ether group, $R^6$ is a divalent hydrocarbon group, and $R^7$ is a hydrogen atom or monovalent hydrocarbon group, and (C) a catalytic amount of a platinum group compound. Component (E) is present in an amount to give 0.5 to 5 mol of the hydrosilyl group per mol of the aliphatic unsaturated group in the composition.

We have found that when a fluorinated amide compound having at least two aliphatic unsaturated groups in a molecule and represented by formula (1) or (4) is blended with a fluorinated organohydrogensiloxane as a crosslinking agent or chain extending agent and further with a platinum group compound as a catalyst, the resulting curable composition readily cures at room temperature into cured products having improved solvent resistance, chemical resistance and heat resistance.

BEST MODE FOR CARRYING OUT THE INVENTION

Figure 1:
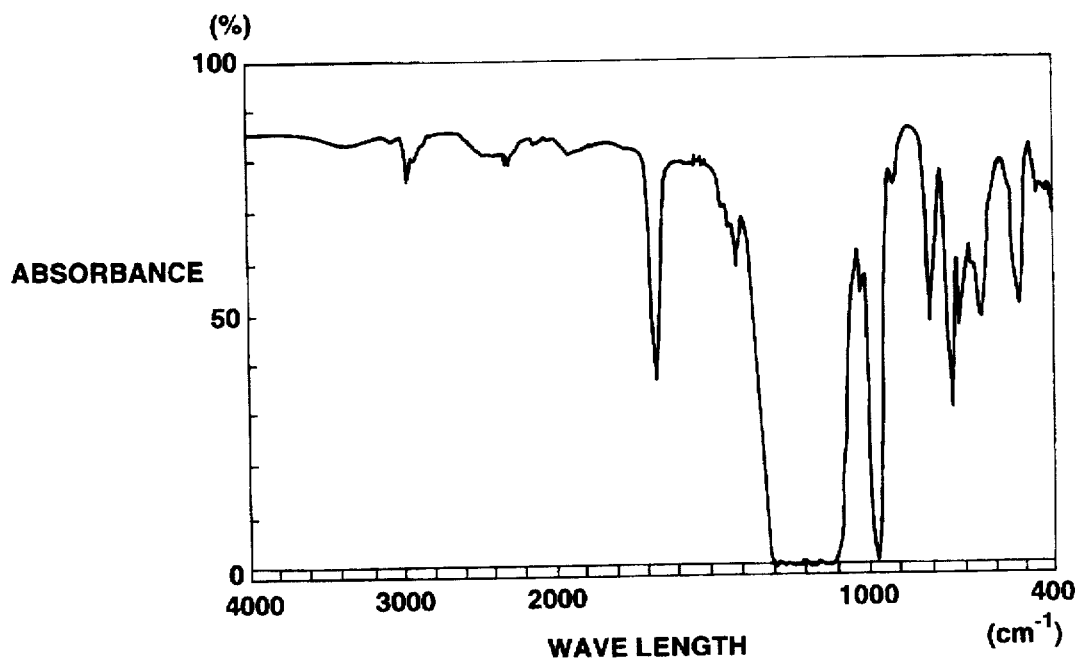
FIG. 1 is an IR spectrum chart of an organic fluorine compound prepared in Example 1.

The organic fluorine compound of the present invention is represented by the general formula (1).

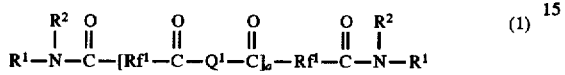

$R^1$ and $R^2$ in formula (1) are independently selected from substituted or unsubstituted monovalent hydrocarbon groups, preferably having 1 to 10 carbon atoms, more preferably 1 to 8 carbon atoms, for example, alkyl groups such as methyl, ethyl, propyl, isopropyl, butyl, isobutyl, tert-butyl, pentyl, neopentyl, hexyl, heptyl, octyl, nonyl and decyl; cycloalkyl groups such as cyclopentyl, cyclohexyl, and cycloheptyl; alkenyl groups such as vinyl, allyl, propenyl, isopropenyl, butenyl, isobutenyl, hexenyl, and cyclohexenyl; aryl groups such as phenyl, tolyl, xylyl, and naphthyl; aralkyl groups such as benzyl, phenylethyl, and phenylpropyl; and substituted ones of these groups wherein some or all of the hydrogen atoms are replaced by halogen atoms including fluorine, chlorine and bromine, such as chloromethyl, bromoethyl, chloropropyl, and trifluoropropyl.

In particular, $R^1$ in formula (1) is preferably a monovalent hydrocarbon group of 2 to 10 carbon atoms, especially 1 to 8 carbon atoms having an aliphatic unsaturated group, for example, an alkenyl group such as vinyl, allyl, propenyl, isopropenyl, butenyl, isobutenyl, hexenyl; a cycloalkenyl group such as cyclohexenyl; and an alkenyl-substituted aryl group such as styryl.

$Q^1$ in formula (1) is a group represented by the following general formula (2) or (3).

$R^2$ in formula (2) is as defined above. $R^3$ is a substituted or unsubstituted divalent hydrocarbon group, preferably having 1 to 20 carbon atoms, more preferably 2 to 10 carbon atoms, for example, alkylene groups such as methylene, ethylene, propylene, methylethylene, butylene, and hexamethylene; cycloalkylene groups such as cyclohexylene; arylene groups such as phenylene, tolylene, xylylene, naphthylene, and biphenylene; substituted ones of these groups wherein some or all of the hydrogen atoms are replaced by halogen atoms; and combinations of such substituted or unsubstituted alkylene and/or arylene groups.

The group represented by $R^3$ may have at least one intervening atom within its linkage. The intervening atom is an oxygen, nitrogen or silicon atom. More particularly, the oxygen atom may intervene as —O—. The nitrogen atom may intervene as —NR'—wherein R' is a hydrogen atom, an alkyl group having 1 to 8 carbon atoms, especially 1 to 6 carbon atoms or an aryl group. The silicon atom may intervene as an organosilylene group or as a group containing a linear or cyclic organosiloxane as shown below.

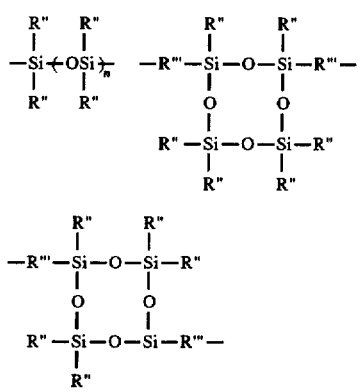

R" is an alkyl group having 1 to 8 carbon atoms or aryl group as exemplified for $R^2$, R'" is an alkylene group having 1 to 6 carbon atoms or arylene group as exemplified for $R^3$, and n is an integer of 0 to 10, especially 0 to 5.

Examples of the group having an intervening O, N or Si atom represented by $R^3$ are given below.

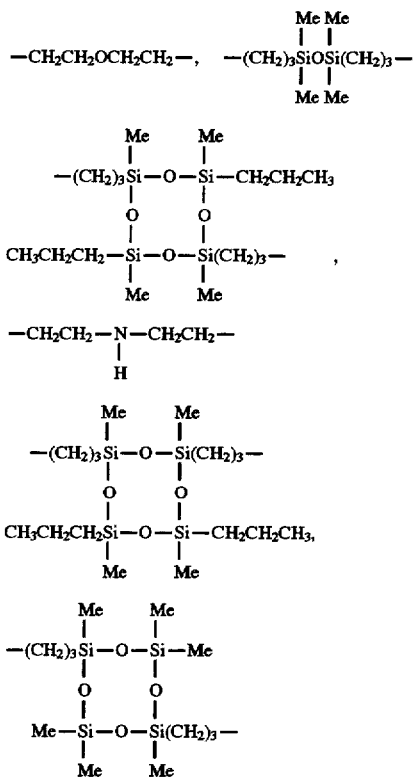

Me: Methyl $R^4$ and $R^5$ in formula (3) are independently selected from substituted or unsubstituted divalent hydrocarbon groups, preferably having 1 to 10 carbon atoms, more preferably 2 to 6 carbon atoms, for example, alkylene groups such as methylene, ethylene, propylene, methylethylene, butylene, and hexamethylene, cycloalkylene groups such as cyclohexylene and substituted ones of these groups wherein some or all of the hydrogen atoms are replaced by halogen atoms.

Examples of the group of formula (2) or (3) represented by Q1 in formula (1) are given below. Note that in the following chemical formulae, Me is methyl and Ph is phenyl.

$$-\underset{\underset{Me}{|}}{N}(CH_2)_2\underset{\underset{Me}{|}}{N}-, \quad -\underset{\underset{Ph}{|}}{N}(CH_2)_6\underset{\underset{Ph}{|}}{N}-$$

$$-N\begin{array}{c}CH_2-CH_2\\ \\CH_2-CH_2\end{array}N-, \quad -N\begin{array}{c}CH(CH_3)-CH_2\\ \\CH_2-CH(CH_3)\end{array}N-$$

$$-\underset{\underset{Me}{|}}{N}CH_2-\!\!\!\bigcirc\!\!\!-CH_2\underset{\underset{Me}{|}}{N}-, \quad -\underset{\underset{Me}{|}}{N}-\!\!\!\bigcirc\!\!\!-\underset{\underset{Me}{|}}{N}-$$

$$-\underset{\underset{Me}{|}}{N}(CH_2)_3-\underset{\underset{Me}{|}}{\overset{\overset{Me}{|}}{Si}}-O-\underset{\underset{Me}{|}}{\overset{\overset{Me}{|}}{Si}}-(CH_2)_3\underset{\underset{Me}{|}}{N}-,$$

$$-\underset{\underset{}{|}}{N}CH_2CH_2CH_2-\underset{\underset{O}{|}}{\overset{\overset{Ph}{|}}{Si}}-O-\underset{\underset{O}{|}}{\overset{\overset{Me}{|}}{Si}}-CH_2CH_2CH_3$$
$$CH_3CH_2CH_2-\underset{\underset{Me}{|}}{\overset{\overset{|}{|}}{Si}}-O-\underset{\underset{Me}{|}}{\overset{\overset{Ph}{|}}{Si}}-CH_2CH_2CH_2\underset{\underset{}{|}}{N}-$$

$$-\underset{\underset{}{|}}{N}CH_2CH_2CH_2-\underset{\underset{O}{|}}{\overset{\overset{CH_3}{|}}{Si}}-O-\underset{\underset{O}{|}}{\overset{\overset{CH_3}{|}}{Si}}-CH_2CH_2CH_3$$
$$CH_3CH_2CH_2-\underset{\underset{Me}{|}}{\overset{\overset{|}{|}}{Si}}-O-\underset{\underset{Me}{|}}{\overset{\overset{Me}{|}}{Si}}-CH_2CH_2CH_2\underset{\underset{}{|}}{N}-$$

$$-\underset{\underset{}{|}}{N}CH_2CH_2-Rf^1-CH_2CH_2\underset{\underset{}{|}}{N}-$$

(Rf$^1$ is as defined above.)

In formula (1), Rf$^1$ is a divalent perfluoroalkylene or perfluoropolyether group. The divalent perfluoroalkylene group is preferably represented by the formula:

$$-C_mF_{2m}-$$

wherein m=1 to 10, preferably 1 to 6. The divalent perfluoropolyether group is preferably represented by the following formulae:

$$-(CFOCF_2)_p-(CF_2)_r-(CF_2OCF)_q-$$
$$\quad\ |\qquad\qquad\qquad\qquad\ |$$
$$\quad\ X\qquad\qquad\qquad\qquad\ X$$

wherein X is F or CF$_3$ group, p, q and r are integers in the range: $p \geq 1$, $q \geq 1$, and $2 \leq p+q \leq 200$, especially $3 \leq p+q \leq 110$ and $0 \leq r \leq 6$, $$-CF_2CF_2OCF_2-(CFOCF_2)_s-(CF_2)_r-(CF_2OCF)_t-CF_2OCF_2CF_2-$$
$$\qquad\qquad\qquad\ |\qquad\qquad\qquad\qquad\ |$$
$$\qquad\qquad\qquad\ CF_3\qquad\qquad\qquad\qquad CF_3$$

wherein r, s and t are integers in the range: $0 \leq r \leq 6$, $s \geq 0$, $t \geq 0$, and $2 \leq s+t \leq 200$, especially $3 \leq s+t \leq 110$, $$-CF-(OCFCF_2)_u-(OCF_2)_v-OCF-$$
$$\ |\qquad\ |\qquad\qquad\ |$$
$$\ X\qquad\ X\qquad\qquad X$$

wherein X is F or CF$_3$ group, u and v are integers in the range: $1 \leq u \leq 20$ and $1 \leq v \leq 20$, and $$-CF_2CF_2-(OCF_2CF_2CF_2)_w-OCF_2CF_2-$$

wherein w is an integer in the range: $1 \leq w \leq 20$.

Examples of Rf$^1$ are given below.

$$-C_4F_8-, \quad -C_8F_{12}-, \quad -(CFOCF_2)_3(CF_2OCF)_2-$$
$$\qquad\qquad\qquad\qquad\qquad\ |\qquad\qquad\quad\ |$$
$$\qquad\qquad\qquad\qquad\qquad CF_3\qquad\qquad CF_3$$

$$-(CFOCF_2)_{15}(CF_2OCF)_{15}-, \quad -(CFOCF_2)_m(CF_2OCF)_n-$$
$$\quad\ |\qquad\qquad\quad\ |\qquad\qquad\qquad\quad\ |\qquad\qquad\quad\ |$$
$$\ CF_3\qquad\qquad CF_3\qquad\qquad\qquad CF_3\qquad\qquad CF_3$$
$$\qquad\qquad\qquad\qquad\qquad\qquad\qquad\overline{n+m}=38$$

$$-CF_2CF_2OCF_2(CF_2)_2CF_2OCF_2CF_2-,$$

$$-CF_2CF_2OCF_2CFOCF_2(CF_2)_2CF_2OCFCF_2OCF_2CF_2-,$$
$$\qquad\qquad\qquad\ |\qquad\qquad\qquad\qquad\ |$$
$$\qquad\qquad\qquad CF_3\qquad\qquad\qquad\quad CF_3$$

$$-CF_2CF_2OCF_2CFOCF_2(CF_2)_2CF_2OCFCF_2OCF_2CF_2-,$$
$$\qquad\qquad\qquad\ |\qquad\qquad\qquad\qquad\ |$$
$$\qquad\qquad\qquad CF_3\qquad\qquad\qquad\quad CF_3$$

$$-CF_2(OCF_2CF_2)_n(OCF_2)_mOCF_2-, \quad -CF(OCFCF_2)_n(OCF_2)_mOCF-,$$
$$\qquad\qquad\qquad\qquad\qquad\qquad\qquad\qquad\ |\qquad\ |\qquad\qquad\ |$$
$$\qquad\qquad\qquad\qquad\qquad\qquad\qquad\qquad CF_3\ CF_3\qquad\qquad CF_3$$

$\overline{n}=5$–40, typically 8 $\qquad\qquad\overline{n}=5$–50, typically 15
$\overline{m}=1$–10, typically 2 $\qquad\quad\overline{m}=1$–10, typically 2

$$-CF_2CF_2(OCF_2CF_2CF_2)_nOCF_2CF_2-,$$

$\overline{n}=5$–100, typically 10

$$-(CFOCF_2)_n(CF_2OCF)_m-\qquad, \quad -(CFOCF_2)_n(CF_2OCF)_m-$$
$$\quad\ |\qquad\qquad\quad\ |\qquad\qquad\qquad\qquad\ |\qquad\qquad\quad\ |$$
$$\ CF_3\qquad\qquad CF_3\qquad\qquad\qquad\quad CF_3\qquad\qquad CF_3$$
$\overline{n+m}=2$–200, preferably 30–110 $\quad\overline{n+m}=20$–110, typically 30

In formula (1), letter a is an integer inclusive of 0. The organic fluorine compound of formula (1) contains at least one divalent perfluoroalkylene or perfluoropolyether group while letter a is preferably an integer of 0 to 10, more preferably equal to 0, 1, 2, 3, 4, 5 or 6.

The organic fluorine compounds of formula (1) according to the invention may be used in various forms covering from low viscosity polymers having a viscosity of several tens of centistokes at 25° C. to solid raw rubber-like polymers. For ease of handling, raw rubber-like polymers are preferred for the intended application as heat vulcanizable rubber and polymers having a viscosity of about 100 to about 100,000 centistokes at 25° C. are preferred for the intended application as liquid rubber. Too low viscosity would be undesirable because cured products would have low elongation as elastomers and imbalance of physical properties.

The organic fluorine compounds or fluorinated amide compounds of formula (1) can be obtained by the following method. The fluorinated amide compound of formula (1) wherein letter a is equal to 0 can be synthesized by reacting a compound having an acid fluoride group at either end of the following general formula (7) with a secondary amine compound of the following general formula (8) in the presence of an acid acceptor such as trimethylamine.

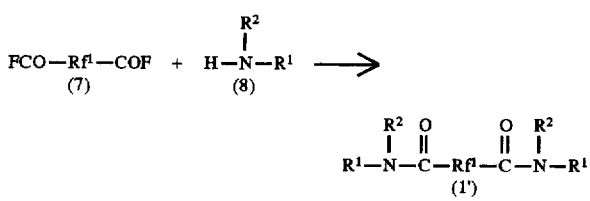

Note that $R^1$, $R^2$ and $Rf^1$ are as defined previously.

Also the fluorinated amide compound of formula (1) wherein letter a is an integer of at least 1 can be synthesized by reacting a compound having an acid fluoride group at either end of formula (7) with a compound having an amino group at either end of the following general formula (9):

 (9)

wherein $Q^1$ is as defined previously in the presence of an acid acceptor and further reacting with a secondary amine compound of formula (8).

Although the compound having an acid fluoride group at either end of formula (7) and the secondary amine compound of formula (8) may be used in an desired ratio, it is preferred that the molar ratio of the charge (a) of the formula (7) compound to the charge (b) of the formula (8) compound, (a)/(b), range from 0.5 mol/mol to 2 mol/mol.

Also the compound of formula (7) and the compound of formula (9) are mixed such that the molar charge (a) of the formula (7) compound is not less than the molar charge (c) of the formula (9) compound. The number (represented by a) of recurring units in formula (1) may be controlled to an appropriate value by adjusting the molar ratio (a)/(c). Higher values of (a)/(c) allow for synthesis of polymers having a relatively low molecular weight whereas molar ratios (a)/(c) approximating to 1 allow for synthesis of polymers having a high molecular weight.

Reaction conditions are not critical. Preferred conditions include a temperature of 20 to 100° C. and a time of about 1 to 8 hours, more preferably a temperature of 20 to 50° C. and a time of about 2 to 4 hours.

Among the fluorinated amide compounds of formula (1), those fluorinated amide compounds wherein $Q^1$ is a group having an intervening silicon atom can be synthesized by selecting a secondary amine compound of formula (8) wherein $R^1$ is an allyl group and having an aliphatic unsaturated group such as $HR^2N$—$CH_2CH=CH_2$, subjecting it to the above-mentioned reaction to form a compound having an allyl group at either end of the following general formula (10), and further reacting the compound of formula (10) with a compound of the following general formula (11) in the presence of an addition reaction catalyst.

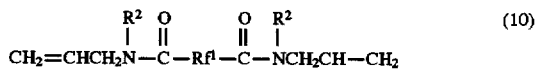 (10)

Note that $R^2$ and $Rf^1$ are as previously defined.

——H (11)

Note that P represents a group as exemplified below.

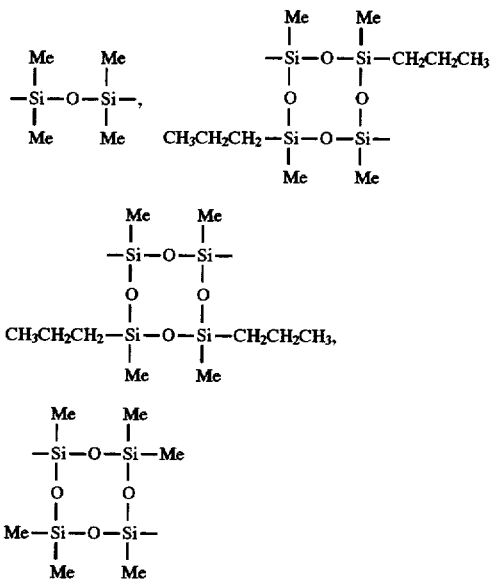

In this reaction, the compound having an allyl group at either end of formula (10) and the compound of formula (11) are mixed such that the molar charge (d) of the formula (10) compound does not exceed the molar charge (e) of the formula (11) compound. The molar ratio (d)/(e) is at most 2. That is, 1<(d)/(e)≦2. Within this range, higher values of (d)/(e) allow for synthesis of polymers having a relatively low molecular weight whereas molar ratios (d)/e) approximating to 1 allow for synthesis of polymers having a high molecular weight.

The catalyst used herein is selected from the elements of Group VIII in the Periodic Table and compounds thereof, for example, chloroplatinic acid, alcohol-modified chloroplatinic acid (see U.S. Pat. No. 3,220,972), complexes of chloroplatinic acid with olefins (see U.S. Pat. Nos. 3,159,601, 3,159,662 and 3,775,452), platinum black and palladium on supports such as alumina, silica and carbon, rhodium-olefin complexes, and chlorotris (triphenylphosphine)rhodium (Wilkinson catalyst). It is used in a catalytic amount. The complexes are preferably used as solution in suitable solvents such as alcohol, ketone, ether and hydrocarbon solvents.

Preferably the reaction is effected at about 50° to 150° C., especially about 80° to 120° C., for about 2 to 4 hours.

The organic fluorine compounds of the present invention can form elastomers having a high fluorine content and low surface energy, which will find use in a variety of applications as raw materials, for example, stock materials for rubber materials having chemical and solvent resistance and base components for mold release agents. For example, elastomers can be obtained by reacting a polymer of an organic fluorine compound blocked with an alkenyl group at either end with a compound having at least three hydrosilyl groups in a molecule in the presence of an addition reaction catalyst. These elastomers exhibit high solvent and chemical resistance because of high fluorine contents and are improved in mold release and water repellency because of low surface energy. Then the elastomers are useful as sealants, molded parts, extruded parts, coating materials and mold release agents.

Also contemplated herein is a curable composition comprising an organic fluorine compound or fluorinated amide compound of formula (1) defined above. The present invention further provides a curable composition comprising a fluorinated amide compound of formula (4) which will be defined later.

These curable compositions are now described in detail.

The first curable composition of the invention contains components (A), (B) and (C) as essential components. Component (A) is an organic fluorine compound or fluorinated amide compound of formula (1) defined above. The fluorinated amide compound as component (A) should have at least two aliphatic unsaturated groups in a molecule. In this regard, a fluorinated amide compound of formula (1) wherein $R^1$ is a monovalent hydrocarbon group having 1 to 10 carbon atoms and an aliphatic unsaturated group, especially an alkenyl group having 1 to 8 carbon atoms is preferably used in the first curable composition.

Component (B) of the first curable composition is a fluorinated organohydrogensiloxane which serves as a crosslinking agent and chain extender for the fluorinated amide compound (A). The fluorinated organohydrogensiloxane (B) should contain at least one monovalent perfluoroalkyl ether or perfluoroalkyl group and at least two, typically 2 to 50, especially 3 to 20 hydrosilyl (SiH) groups in a molecule. The monovalent perfluoroalkyl ether and perfluoroalkyl groups are preferably those represented by the following general formulae:

$$C_mF_{2m+1}-$$

wherein m is an integer of 1 to 10, preferably 2 to 10, and

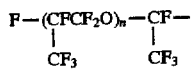

wherein n is an integer of 1 to 5.

The fluorinated organohydrogensiloxanes may be of cyclic or chain structure or three-dimensional network. They preferably have at least one monovalent organic group having a perfluoroalkyl or perfluoroalkyl ether group of the following general formula in a molecule as a monovalent substituent attached to a silicon atom.

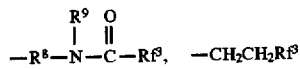

In the formulae, $R^8$ is a divalent hydrocarbon group, preferably having 1 to 6 carbon atoms, for example, alkylene groups such as methylene, ethylene, propylene, methylethylene, tetramethylene, and hexamethylene, $R^9$ is a hydrogen atom or a monovalent hydrocarbon group, preferably having 1 to 8 carbon atoms, more preferably 1 to 6 carbon atoms as defined for $R^2$, and $Rf^3$ is a monovalent perfluoroalkyl or perfluoroalkyl ether group as previously exemplified.

The fluorinated organohydrogensiloxane (B) has a monovalent substituent group attached to a silicon atom other than the monovalent organic group having a perfluoroalkyl or perfluoroalkyl ether group. Examples of the other substituent group include monovalent hydrocarbon groups free of an aliphatic unsaturated bond, preferably having 1 to 10 carbon atoms, more preferably 1 to 8 carbon atoms as previously defined for $R^2$.

The number of silicon atoms per molecule of the fluorinated organohydrogensiloxane is not critical although it generally has about 2 to 50, preferably about 4 to 30 silicon atoms.

Examples of the fluorinated organohydrogensiloxane are given below. They may be used alone or in admixture of two or more.

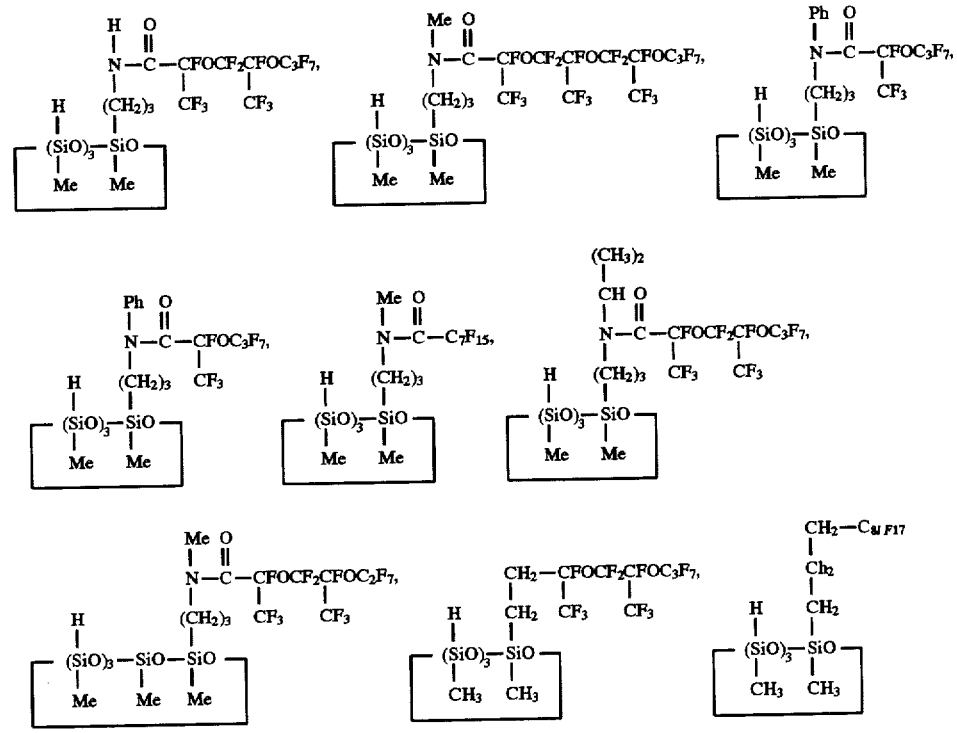

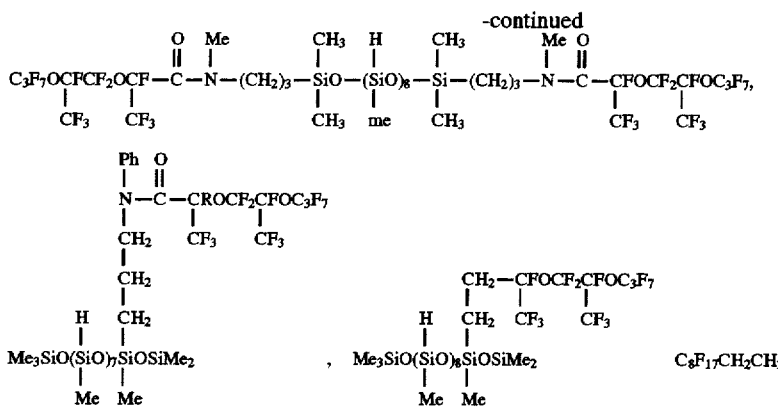

When the fluorinated organohydrogensiloxane used as component (B) is compatible with the fluorinated amide compound as component (A), the resulting curable composition will yield a uniform cured product.

Component (B) is blended in the composition in such an amount as to provide 0.5 to 5 mol, preferably 1 to 2 mol of the hydrosilyl group (i.e., Si-H group) in component (B) per mol of the aliphatic unsaturated group (e.g., vinyl, allyl and cycloalkenyl groups) in the entire composition, especially component (A). Less than 0.5 mol of the hydrosilyl group on this basis will lead to an insufficient degree of crosslinking. With more than 5 mol of the hydrosilyl group, chain lengthening will become predominant, resulting in short curing or foaming and adversely affecting heat resistance and compression set. Most often, components (A) and (B) are blended such that about 0.1 to 50 parts by weight of component (B) is available per 100 parts by weight of component (A).

The first curable composition further contains a platinum group compound as an essential component (C). It is a catalyst for catalyzing addition reaction or hydrosilylation between the fluorinated amide compound and the fluorinated organohydrogensiloxane, that is, serves as a curing promoter. Since the platinum group compounds are generally compounds of noble metals and expensive, relatively easily available platinum compounds are often used.

Illustrative, non-limiting examples of the platinum compound include chloroplatinic acid, complexes of chloroplatinic acid with olefins such as ethylene, complexes of chloroplatinic acid with alcohols or vinylsiloxanes, and platinum on silica, alumina and carbon. Platinum group compounds other than the platinum compounds are also useful. Known examples include compounds of rhodium, ruthenium, iridium, and palladium, for example, such as $RhCl(PPh_3)_3$, $RhCl(CO)(PPh_3)_2$, $RhCl(C_2H_4)_2$, $Ru_3(CO)_{12}$, $IrCl(CO)(PPh_3)_2$, and $Pd(PPh_3)_4$ wherein Ph is phenyl.

On use, these catalysts may be used in solid form if they are solid catalysts. In order to form more uniform cured products, a solution of chloroplatinic acid or its complex in a suitable solvent is preferably used as a miscible mixture with the fluorinated amide compound (A).

The amount of the catalyst used is not critical. A desired curing rate will be achieved with a catalytic amount. From an economical point of view or to produce satisfactory cured products, the catalyst is preferably added in an amount of about 1 to 1,000 ppm, more preferably about 10 to 500 ppm of platinum group element based on the weight of the entire curable composition.

Like the first curable composition of the present invention containing essential components (A), (B) and (C), the second curable composition of the present invention contains components (D), (E) and (C) as essential components. Component (D) is a fluorinated amide compound of formula (4) to be defined later. Component (E) is a fluorinated organohydrogensiloxane to be defined later. Component (C) is a platinum group compound which is the same as in the first curable composition.

Instead of the fluorinated amide compound of formula (1) as component (A), the second curable composition of the invention uses a fluorinated amide compound having at least two aliphatic unsaturated groups in a molecule of the following general formula (4) as component (D).

$$R^1-N-C-[Rf^1-C-Q^2-C]_a-Rf^1-C-N-R^1 \quad (4)$$
(with H, O, O, O, O, H on respective atoms)

In formula (4), $R^1$, $Rf^1$ and a are as previously defined in formula (1). Preferably $R^1$ is an aliphatic unsaturated group having 1 to 10 carbon atoms, especially an alkenyl group having 1 to 8 carbon atoms.

$Q^2$ is a group represented by the following general formula (5):

$$-N-R^3-N- \quad (5)$$
(with H, H on the N atoms)

wherein $R^3$ is as previously defined in formula (2).

Illustrative examples of the group represented by $Q^2$ are given below.

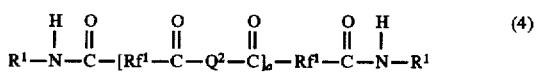

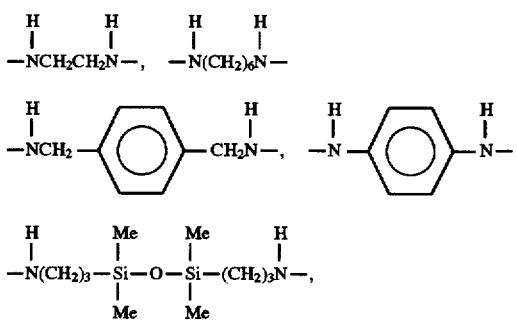

-continued

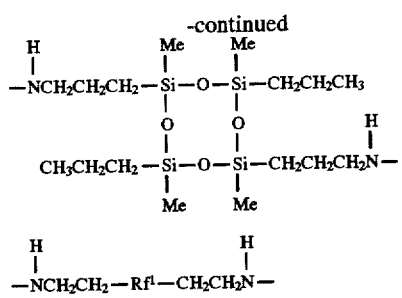

Rf¹ is as previously defined.

With respect to the viscosity of the fluorinated amide compound (D) used herein, the same as described for the fluorinated amide compound (A) applies.

The fluorinated amide compound as component (D) can be synthesized by reacting a compound having an ester group at either end of the general formula (12):

$$CH_3OCO-Rf^1-COOCH_3 \tag{12}$$

wherein Rf¹ is as previously defined with a compound of the general formula (13):

$$H-Q^2-H \tag{13}$$

wherein $Q^2$ is as previously defined.

The compound of formula (12) and the compound of formula (13) are mixed such that the molar charge (f) of the formula (12) compound is not less than the molar charge (g) of the formula (13) compound. The number (represented by a) of recurring units in formula (4) may be controlled to an appropriate value by adjusting the molar ratio (f)/(g). Higher values of (f)/(g) allow for synthesis of polymers having a relatively low molecular weight whereas molar ratios (f)/(g) approximating to 1 allow for synthesis of polymers having a high molecular weight.

Reaction conditions are not critical. Preferred conditions include a temperature of 20 to 100° C. and a time of about 1 to 8 hours, more preferably a temperature of 20° to 50° C. and a time of about 2 to 4 hours.

Component (E) of the second curable composition is a fluorinated organohydrogensiloxane which contains at least one monovalent organic group having a monovalent perfluoro-alkyl or perfluoroalkyl ether group of the following general formula (6) and at least two, typically 2 to 50, especially 3 to 20 hydrosilyl (SiH) groups in a molecule.

In formula (6), $Rf^2$ is a monovalent perfluoroalkyl group or monovalent perfluoroalkyl ether group, with their examples being the same as the perfluoroalkyl and perfluoroalkyl ether groups exemplified for $Rf^3$. $R^6$ is a divalent hydrocarbon group having 1 to 8 carbon atoms as exemplified for $R^8$. $R^7$ is a hydrogen atom or a monovalent hydrocarbon group having 1 to 8 carbon atoms, especially 1 to 6 carbon atoms as exemplified for $R^9$.

The fluorinated organohydrogensiloxane (E) has a monovalent substituent group attached to a silicon atom other than the monovalent organic group having a perfluoroalkyl or perfluoroalkyl ether group. Examples of the other substituent group include monovalent hydrocarbon groups free of an aliphatic unsaturated bond, preferably having 1 to 10 carbon atoms, more preferably 1 to 8 carbon atoms as previously defined for $R^2$.

The number of silicon atoms per molecule of the fluorinated organohydrogensiloxane is not critical although it generally has about 2 to 50, preferably about 4 to 30 silicon atoms.

Examples of the fluorinated organohydrogensiloxane (E) are given below. They may be used alone or in admixture of two or more.

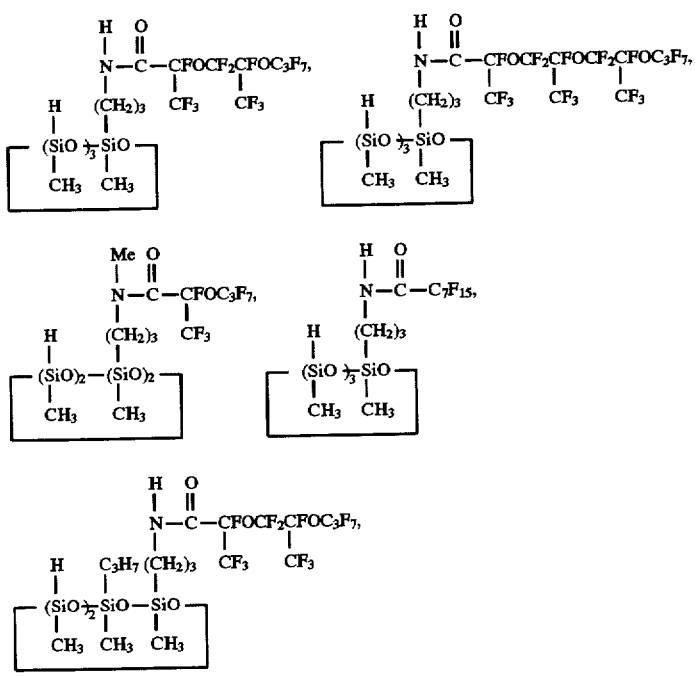

-continued

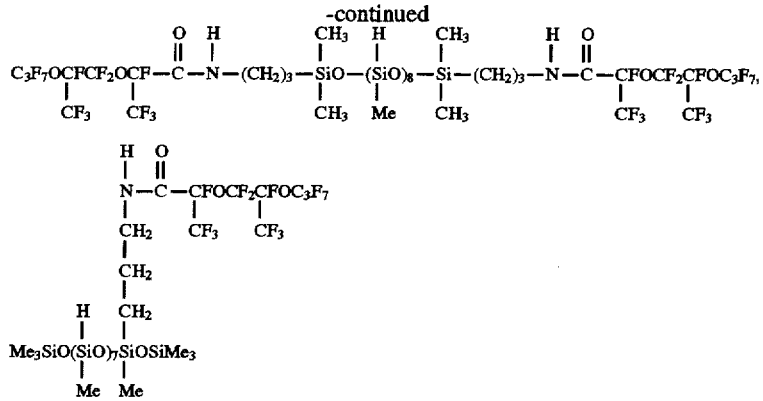

Component (E) is blended in the composition in such an amount as to provide 0.5 to 5 mol, preferably 1 to 2 mol of the hydrosilyl group (i.e., Si-H group) in component (E) per mol of the aliphatic unsaturated group (e.g., vinyl, allyl and cycloalkenyl groups) in the entire composition, especially component (D). Less than 0.5 mol of the hydrosilyl group on this basis will lead to an insufficient degree of crosslinking. With more than 5 mol of the hydrosilyl group, chain lengthening will become predominant, resulting in short curing or foaming and adversely affecting heat resistance and compression set. Most often, components (D) and (E) are blended such that about 0.1 to 50 parts by weight of component (E) is available per 100 parts by weight of component (D).

Component (C) in the second curable composition is the same platinum group compound as described for the first curable composition. The amount of component (C) blended is also the same.

Various additives may be added to the first and second curable compositions of the invention in order to enhance their practical usage. Useful additives include polysiloxanes containing a $CH_2=CH(R)SiO$ unit wherein R is a substituted or unsubstituted monovalent hydrocarbon group (see JP-B 10947/1973) and acetylene compounds (see U.S. Pat. No. 3,445,420 and JP-B 3774/1979), which are added for the purpose of controlling the curing rate of the curable composition, and ionic compounds of heavy metals (see U.S. Pat. No. 3,532,649). Where such additives are added, the amount of the fluorinated organohydrogensiloxane blended is determined by taking into account the amount of these additives blended in addition to component (A) or (D). More specifically, 0.5 to 5 mol of Si-H group should be present per mol of the aliphatic unsaturated group (e.g., vinyl, allyl and cycloalkenyl groups) in the entire composition as previously mentioned.

Moreover, fillers may be blended in the curable compositions of the invention for the purposes of reducing thermal shrinkage upon heating, reducing the coefficient of thermal expansion of elastomers as cured, improving thermal stability, weather resistance, chemical resistance, flame retardancy and mechanical strength, and reducing gas permeability. Exemplary fillers include fumed silica, quartz powder, glass fibers, carbon, metal oxides such as iron oxide, titanium oxide, and cerium oxide, and metal carbonates such as calcium carbonate and magnesium carbonate. If desired, suitable pigments, dyes or antioxidants may also be added.

Any desired method may be used in preparing the curable composition according to the invention. The composition can be prepared simply by kneading the above-defined components. The curable composition as kneaded can be cured at room temperature depending on the type of functional group in the fluorinated amide compound as the first essential component and the type of catalyst as the third essential component. Preferably the composition is cured by heating at 100° to 150° C. for several minutes to several hours.

On use, the curable compositions of the invention may be dissolved in suitable fluorinated solvents such as metaxylene hexafluoride and fluorinert to a desired concentration depending on its application and purpose.

The curable compositions of the invention may be used in a variety of applications. Cured products resulting from the curable compositions exhibit high solvent and chemical resistance because of high fluorine contents and are improved in mold release and water repellency because of low surface energy. Then the cured products or elastomers are useful as automotive rubber materials required to be oil resistant, tent film materials, sealants, molded parts, extruded parts, coating materials and mold release agents.

EXAMPLE

Examples of the present invention are given below by way of illustration and not by way of limitation. Note that Me is methyl and Ph is phenyl. All parts are by weight.

Example 1

A 300-ml four-necked flask equipped with a stirrer, thermometer, Dimroth condenser, and dropping funnel was charged with 189.2 g of a compound having an acid fluoride group at each end of the following formula (a) having a viscosity of 430 centistokes at 25° C. With stirring, a mixture of 7.1 g of isopropylallylamine and 6.1 g of triethylamine was added dropwise to the flask at 20° C.

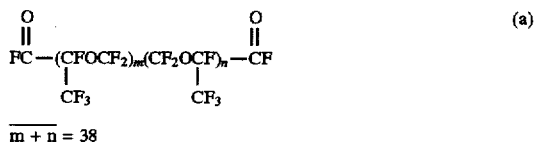

After the dropwise addition, reaction was effected at 60° C. for 2 hours. The reaction mixture was subject to filtration under pressure and the filtrate was vacuum stripped at 120° C./3 mmHg, yielding 189.5 of a compound as a pale yellow clear liquid. The compound had a viscosity of 841 centistokes at 25° C., a specific gravity of 1.832 at 25° C., and a refractive index of 1.3138 at 25° C. The compound was analyzed by IR spectroscopy, with the results shown in FIG. 1. In FIG. 1, the following absorption peaks were observed.

| 1100–1300 cm$^{-1}$ | $v_{C-F}$ |
|---|---|
| 1685 cm$^{-1}$ | $v_{C=O}$ |

The allyl content of this compound was quantitatively determined to be 0.031 mol/100 g. From these data, the compound was identified to be a polymer of an organic fluorine compound represented by the following structural formula (b).

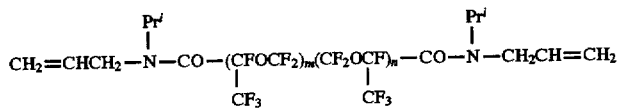

(b)

Pr$^i$ is isopropyl group.

Example 2

A flask as used in Example 1 was charged with 189.2 g of the compound having an acid fluoride group at each end of formula (a) having a viscosity of 430 centistokes at 25° C. With stirring, a mixture of 9.6 g of allylaniline and 6.1 g of triethylamine was added dropwise to the flask at 20° C. through the dropping funnel. Reaction and post-treatment were done as in Example 1, yielding 190.1 of a compound as a pale yellow clear liquid.

Figure 2:
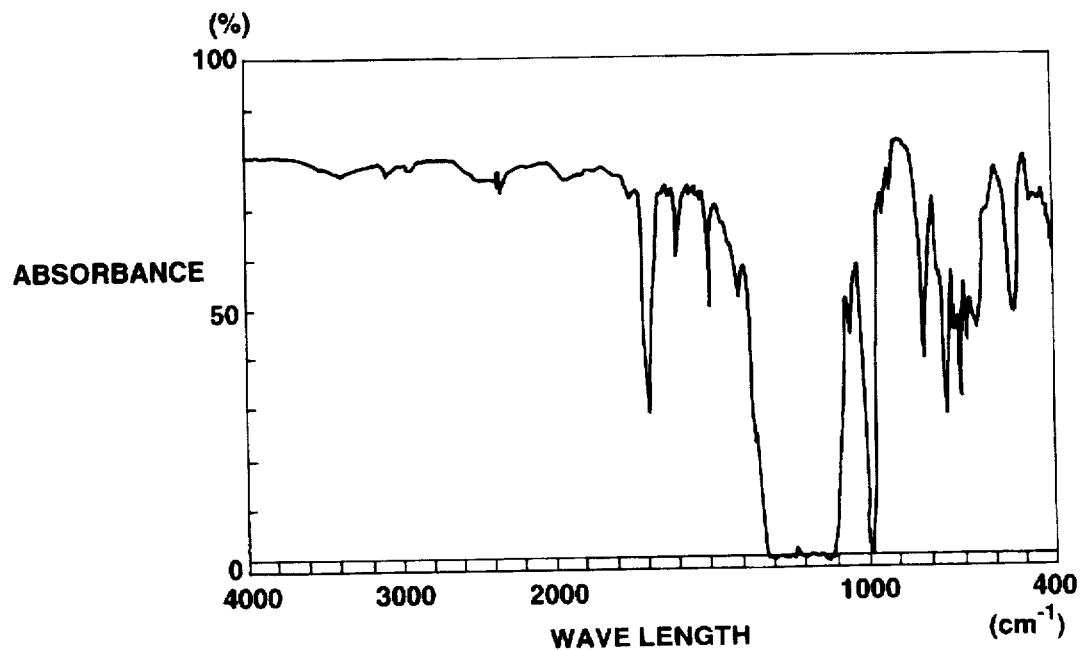
FIG. 2 is an IR spectrum chart of an organic fluorine compound prepared in Example 2.

The compound had a viscosity of 1192 centistokes at 25° C., a specific gravity of 1.841 at 25° C., and a refractive index of 1.3208 at 25° C. The compound was analyzed by IR spectroscopy, with the results shown in FIG. 2. In FIG. 2, the following absorption peaks were observed.

| 1100–1300 cm$^{-1}$ | $v_{C-F}$ |
|---|---|
| 1695 cm$^{-1}$ | $v_{C=O}$ |
| 1600, 1500 cm$^{-1}$ | arom. |

The allyl content of this compound was quantitatively determined to be 0.031 mol/100 g. From these data, the compound was identified to be a polymer of an organic fluorine compound represented by the following structural formula (c).

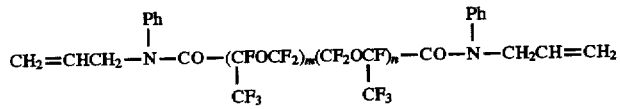

(c)

Note that m and n are as in Example 1.

Example 3

A 200-ml four-necked flask equipped with a stirrer, thermometer, Dimroth condenser, and dropping funnel was charged with 76.9 g of a compound having an acid fluoride group at each end of formula (a) having a viscosity of 430 centistokes at 25° C. With stirring, a mixture of 1.14 g of 2,5-dimethylpiperazine and 2.9 g of triethylamine was added dropwise to the flask at 20° C. through the dropping funnel. After the dropwise addition, reaction was effected at 60° C. for 2 hours. After 0.36 g of methylallylamine was added to the reaction mixture, reaction and post-treatment were done as in Example 1, yielding 72.9 g of a compound as a pale yellow clear liquid.

Figure 3:
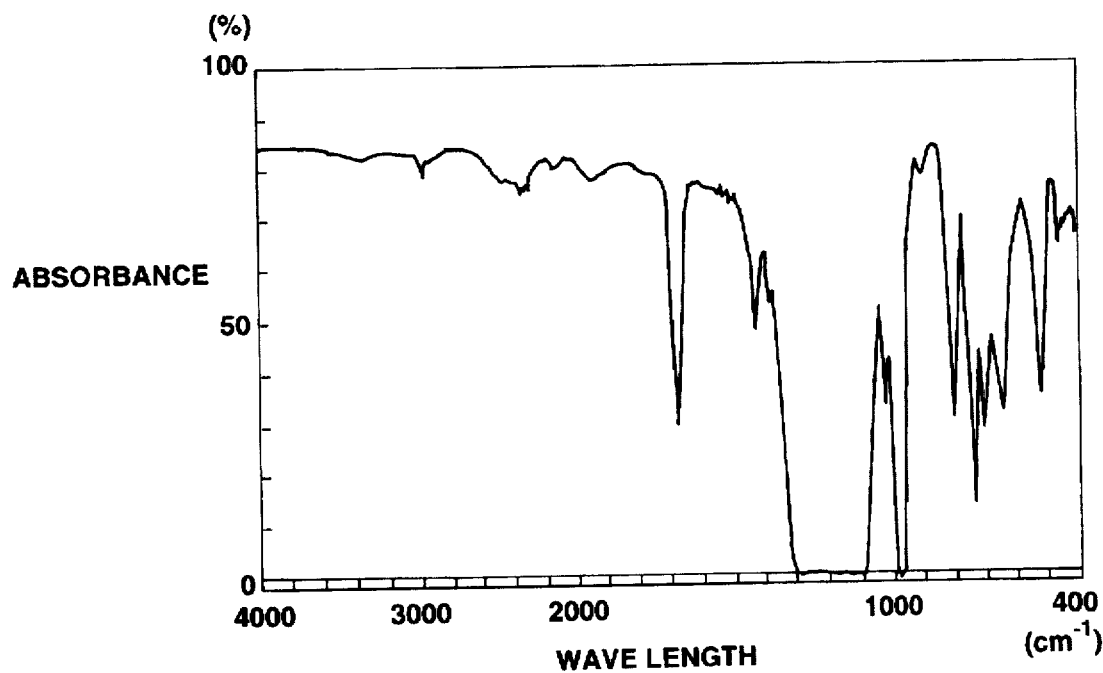
FIG. 3 is an IR spectrum chart of an organic fluorine compound prepared in Example 3.

The compound had a viscosity of 25,200 centistokes at 25° C. The compound was analyzed by IR spectroscopy, with the results shown in FIG. 3. In FIG. 3, the following absorption peaks were observed.

| 1100–1300 cm$^{-1}$ | $v_{C-F}$ |
|---|---|
| 1690 cm$^{-1}$ | $v_{C=O}$ |

The allyl content of this compound was quantitatively determined to be 0.005 mol/100 g. From these data, the compound was identified to be a polymer of an organic fluorine compound represented by the following structural formula (d).

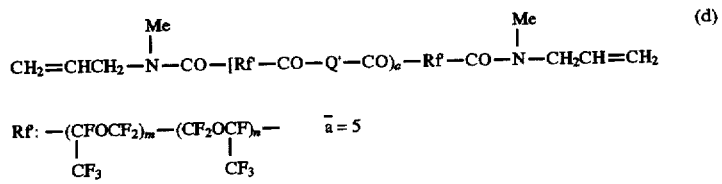

(d)

Q': 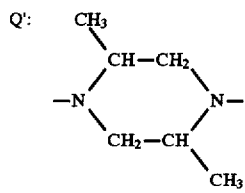

Example 4

A flask as used in Example 3 was charged with 100.0 g of a compound having an allyl group at each end of the following formula (e) having a viscosity of 1,192 centistokes at 25° C. and 50.0 g of meta-xylene hexafluoride. The flask was heated to 90° C. with stirring and 0.1 g of an isopropyl alcohol solution of 2% chloroplatinic acid was added thereto. Then 3.66 g of a cyclotetrasiloxane of the following formula (f) was added dropwise to the flask through the dropping funnel, allowing reaction to take place.

| | |
|---|---|
| 1100–1300 cm$^{-1}$ | $v_{C-F}$ |
| 1690 cm$^{-1}$ | $vC=O$ |
| 1600, 1500 cm$^{-1}$ | arom. |

The compound was quantitatively determined to find an allyl content of 0.007 mol/100 g. From these data, the compound was identified to be a polymer of an organic fluorine compound having the following structural formula (g).

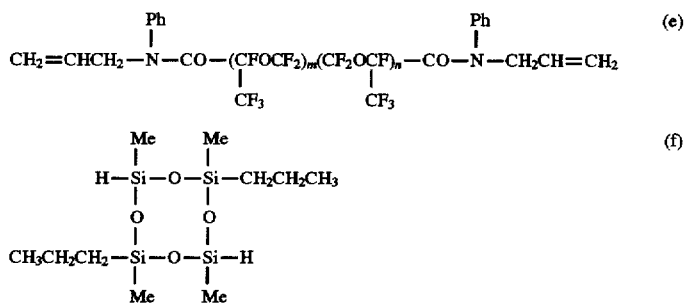

After the dropwise addition, the reaction solution was aged while the disappearance of the cyclotetrasiloxane was confirmed by gas chromatography. Thereafter, the reaction solution was cooled down to room temperature, and 1.5 g of activated carbon was added to the solution which was agitated for 2 hours. The reaction solution was subject to post-treatment as in Example 1, yielding 99.2 g of a clear liquid compound.

Figure 4:
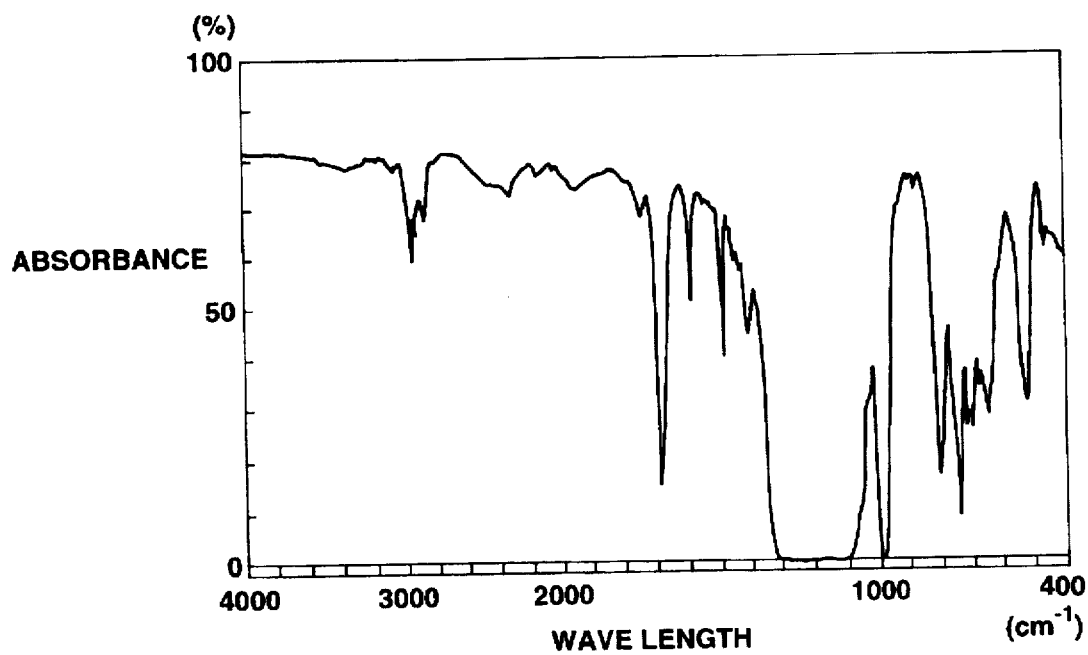
FIG. 4 is an IR spectrum chart of an organic fluorine compound prepared in Example 4.

The compound had a viscosity of 30,700 centistokes at 25° C. It was analyzed by IR spectroscopy, with the results shown in FIG. 4. In FIG. 4, the following absorption peaks were observed.

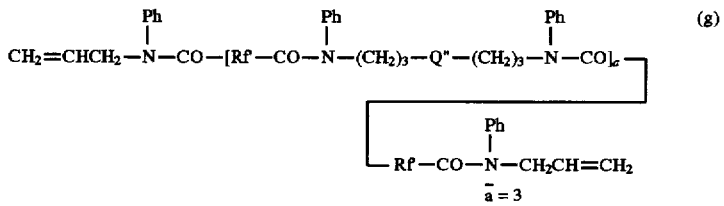

Rf: as defined in Example 3
Q": 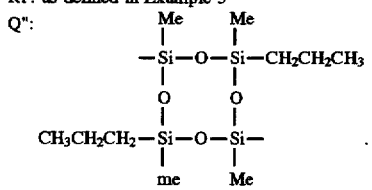

Example 5

A flask as used in Example 1 was charged with 200.0 g of a compound having an acid fluoride group at each end of the following formula (h) having a viscosity of 2,100 centistokes at 25° C. With stirring, a mixture of 3.6 g of allyl aniline and 2.8 g of triethylamine was added dropwise to the flask through the dropping funnel. Reaction and post-treatment were done as in Example 1, yielding 195.1 g of a compound as a pale yellow clear liquid.

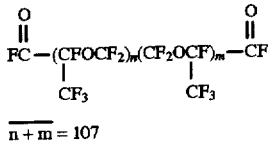

$\overline{n+m} = 107$

Figure 5:
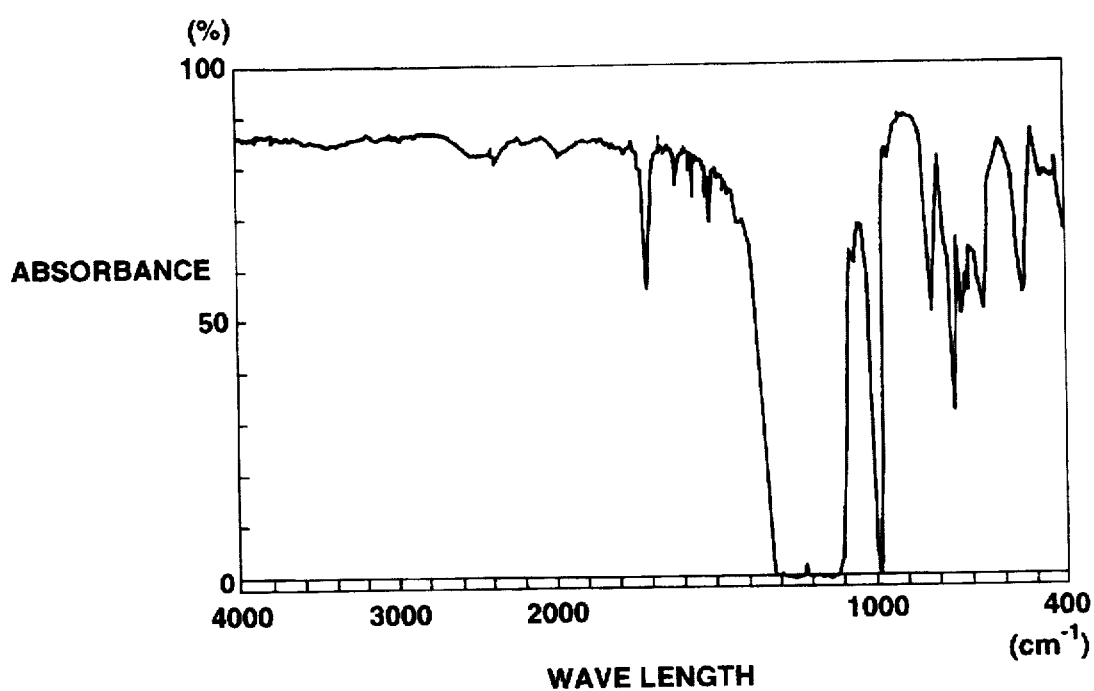
FIG. 5 is an IR spectrum chart of an organic fluorine compound prepared in Example 5.

The compound had a viscosity of 3,300 centistokes at 25° C., a specific gravity of 1.883 at 25° C., and a refractive index of 1.309 at 25° C. It was analyzed by IR spectroscopy, with the results shown in FIG. 5. In FIG. 5, the following absorption peaks were observed.

| 1100–1300 cm$^{-1}$ | $v_{C-F}$ |
|---|---|
| 1705 cm$^{-1}$ | $v_{C=O}$ |
| 1600, 1500 cm$^{-1}$ | arom. |

The compound was quantitatively determined to find an allyl content of 0.011 mol/100 g. From these data, the compound was identified to be a polymer of an organic fluorine compound having the following structural formula (i).

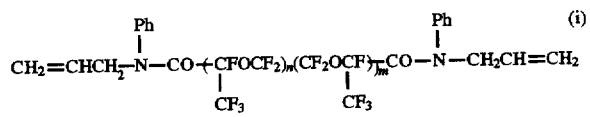

Note that m and n are as defined above.

Example 6

To 100 parts of a polymer of the following formula (j) having a viscosity of 1,190 centistokes at 25° C., an average molecular weight of 7,000 and an allyl content of 0.029 mol/100 g was added 10 parts of fumed silica having a specific surface area of 200 m$_2$/g and treated with trimethylsiloxy group. They were mixed, heat treated, and milled on a three-roll mill. To the compound were further added 10.8 parts of a fluorinated cyclohydrogensiloxane of the following formula (k) and 0.2 part of a toluene solution of a chloroplatinic acid catalyst modified with CH$_2$=CHSiMe$_2$OSiMe$_2$CH=CH$_2$ (platinum concentration 1.0% by weight), with mixing continued.

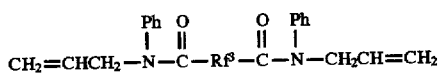

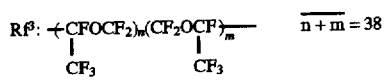

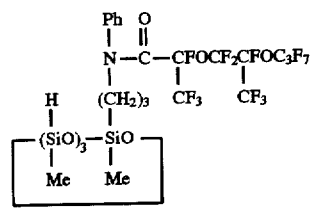

The resulting composition was defoamed under vacuum, placed in a rectangular frame of 2 mm high, deaerated again, and press cured at 120 kg/cm$^2$ and 150° C. for 20 minutes.

A specimen was cut from the cured sheet and measured for physical properties according to JIS K-6301, with the results shown below.

| Hardness (JIS-A) | 43 |
|---|---|
| Elongation (%) | 180 |
| Tensile strength (kgf/cm$^2$) | 25 |

Note that hardness in JIS A scale was measured using a type A spring hardness tester prescribed in JIS K-6301.

The specimen was also examined for heat resistance, solvent swell, chemical resistance, and low-temperature properties. The results are shown in Tables 1 to 4.

TABLE 1

| | Heat resistance | | |
|---|---|---|---|
| | Initial | 3 days | 7 days |
| 150° C. | | | |
| Hardness (JIS-A) | 43 | 58 (+15) | 55 (+12) |
| Elongation (%) | 180 | 160 (−11) | 90 (−50) |
| TS (kgf/cm$^2$) | 25 | 20 (−20) | 27 (+8) |
| Heat loss (%) | — | 0 | 0.3 |
| 200° C. | | | |
| Hardness (JIS-A) | 43 | 60 (+17) | 35 (−8) |
| Elongation (%) | 180 | 90 (−50) | 80 (−56) |
| TS (kgf/cm$^2$) | 25 | 26 (+4) | 24 (−4) |
| Heat loss (%) | — | 0.6 | 0.8 |

Note: Figures in parentheses are percents based on the initial, but increase or decrease of points for hardness.

TABLE 2

| Solvent swell | |
|---|---|
| Solvent | Volume change (%) |
| FuelC | +16 |
| FuelC/methanol = 75/25 | +19 |
| FuelC/methanol = 50/50 | +16 |
| FuelC/methanol = 25/75 | +10 |
| Methanol | +1 |
| Chloroform | +21 |
| Acetone | +14 |
| Toluene | +11 |
| Isopropyl alcohol | +2 |
| Acetonitrile | +3 |
| Methyl ethyl ketone | +17 |
| Ethyl acetate | +19 |
| Tetrahydrofuran | +23 |
| n-hexane | +14 |
| Carbon tetrachloride | +21 |

FuelC: a mixture of toluene and isooctane in a volume ratio of 50/50

TABLE 3

| Chemical resistance (change of rubber hardness) | | |
|---|---|---|
| | Hardness | Surface state |
| Initial | 43 | — |
| conc. hydrochloric acid | 55 (+12) | no change |
| conc. sulfuric acid | 38 (−5) | deteriorated |
| 40% potassium hydroxide | 40 (−3) | no change |

Note: Figures in parentheses are increase or decrease of points.
Deterioration conditions: 20° C./3 days

TABLE 4

| Low-temperature property (German twist test) | |
|---|---|
| $T_2$ | $-20°$ C. |
| $T_5$ | $-31°$ C. |
| $T_{10}$ | $-38°$ C. |
| $T_{100}$ | $-48°$ C. |

Example 7

A composition was prepared by the same procedure as in Example 6 except that 10.6 parts of a fluorinated cyclohydrogensiloxane of the following formula (l) was used instead of the fluorinated cyclohydrogensiloxane of formula (k). A cured sheet was similarly prepared therefrom.

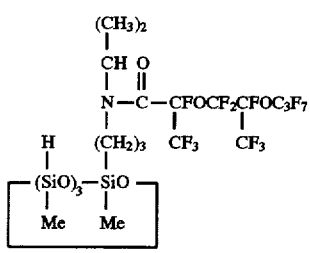

A specimen cut from the cured sheet was similarly measured for physical properties, with the results shown below.

| Hardness (JIS-A) | 40 |
|---|---|
| Elongation (%) | 200 |
| Tensile strength (kgf/cm²) | 22 |

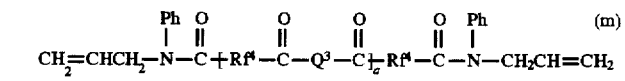

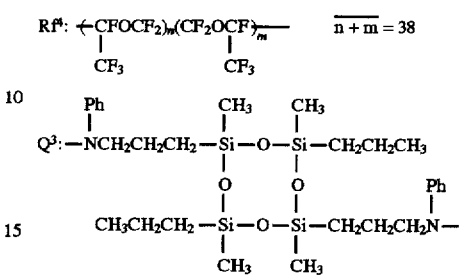

A specimen cut from the cured sheet was similarly measured for physical properties, with the results shown below.

| Hardness (JIS-A) | 33 |
|---|---|
| Elongation (%) | 340 |
| Tensile strength (kqf/cm²) | 45 |

Example 9

A composition was prepared by the same procedure as in Example 6 except that 100 parts of a polymer of the following formula (n) having a viscosity of 13,100 centistokes at 25° C., an average molecular weight of 19,200 and an allyl content of 0.010 mol/100 g was used instead of the polymer of formula (j) and 3.5 parts of the fluorinated cyclohydrogensiloxane in Example 6 was used. A cured sheet was similarly prepared therefrom.

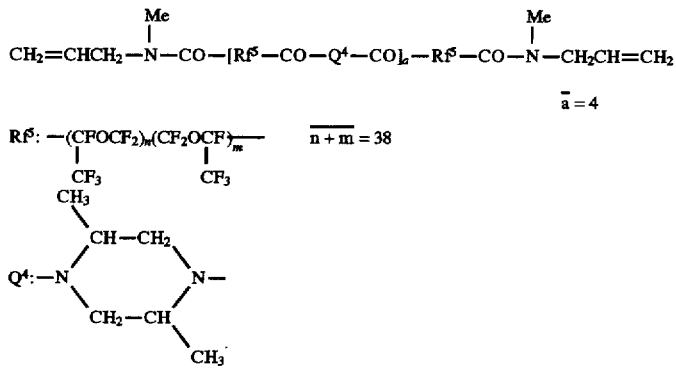

Example 8

A composition was prepared by the same procedure as in Example 6 except that 100 parts of a polymer of the following formula (m) having a viscosity of 28,600 centistokes at 25° C., an average molecular weight of 28,000 and an allyl content of 0.007 mol/100 g was used instead of the polymer of formula (j) and 2.7 parts of the fluorinated cyclohydrogensiloxane in Example 6 was used. A cured sheet was similarly prepared therefrom.

A specimen cut from the cured sheet was similarly measured for physical properties, with the results shown below.

| Hardness (JIS-A) | 45 |
|---|---|
| Elongation (%) | 280 |
| Tensile strength (kgf/cm²) | 53 |

Example 10

A composition was prepared by the same procedure as in Example 6 except that 100 parts of a polymer of the following formula (o) having a viscosity of 2,900 centistokes at 25° C., an average molecular weight of 6,000 and an allyl content of 0.033 mol/100 g was used instead of the polymer of formula (j) and 10.8 parts of a fluorinated cyclohydrogensiloxane of the following formula (p) was used instead of the fluorinated cyclohydrogensiloxane in Example 6. A cured sheet was similarly prepared therefrom.

  (o)

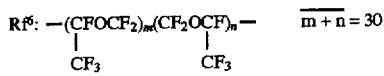  m + n = 30

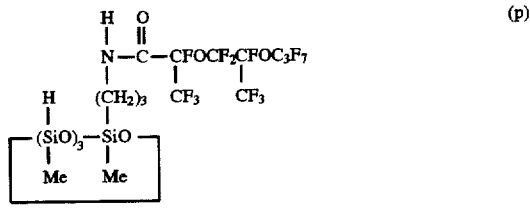  (p)

A specimen cut from the cured sheet was similarly measured for physical properties, with the results shown below.

| Hardness (JIS-A) | 47 |
|---|---|
| Elongation (%) | 310 |
| Tensile strength (kgf/cm²) | 46 |

The specimen was also examined for heat resistance, solvent swell, chemical resistance, and low-temperature properties. The results are shown in Tables 5 to 8.

TABLE 5

| | Heat resistance | | |
|---|---|---|---|
| | Initial | 3 days | 7 days |
| 150° C. | | | |
| Hardness (JIS-A) | 47 | 54 (+7) | 46 (−1) |
| Elongation (%) | 310 | 160 (−48) | 83 (−73) |
| TS (kgf/cm²) | 46 | 40 (−13) | 17 (−63) |
| Heat loss (%) | — | 0.4 | 2.0 |
| 200° C. | | | |
| Hardness (JIS-A) | 47 | 35 (−12) | 35 (−12) |
| Elongation (%) | 310 | 85 (−73) | 69 (−78) |
| TS (kgf/cm²) | 46 | 11 (−76) | 11 (−76) |
| Heat loss (%) | — | 3.9 | 4.4 |

Note: Figures in parentheses are percents based on the initial, but increase or decrease of points for hardness.

TABLE 6

| | Solvent swell | |
|---|---|---|
| Solvent | Weight change (%) | Volume change (%) |
| FuelC | 3 | 6 |
| FuelC/methanol = 75/25 | 5 | 13 |
| FuelC/methanol = 50/50 | 6 | 11 |
| FuelC/methanol = 25/75 | 5 | 10 |
| Methanol | 2 | 4 |
| Chloroform | 7 | 7 |
| Acetone | 5 | 11 |
| Toluene | 2 | 3 |
| Isopropyl alcohol | 3 | 7 |
| Acetonitrile | 1 | 1 |
| Methyl ethyl ketone | 5 | 12 |

TABLE 6-continued

| | Solvent swell | |
|---|---|---|
| Solvent | Weight change (%) | Volume change (%) |
| Ethyl acetate | 6 | 12 |
| Tetrahydrofuran | 7 | 15 |
| n-hexane | 2 | 5 |
| Carbon tetrachloride | 7 | 7 |

FuelC: a mixture of toluene and isooctane in a volume ratio of 50/50

TABLE 7

| | Chemical resistance (solvent swell) | |
|---|---|---|
| | Initial | 3 days |
| conc. hydrochloric acid | | |
| Hardness (JIS-A) | 47 | 53 (+6) |
| Elongation (%) | 310 | 140 (−55) |
| Tensile strength (kgf/cm²) | 46 | 35 (−24) |
| Surface state | — | no change |
| conc. sulfuric acid | | |
| Hardness (JIS-A) | 47 | 32 (−15) |
| Elongation (%) | 310 | 21 (−93) |
| Tensile strength (kgf/cm²) | 46 | 5.3 (−88) |
| Surface state | — | deteriorated |
| 40% potassium hydroxide | | |
| Hardness (JIS-A) | 47 | 44 (−3) |
| Elongation (%) | 310 | 270 (−13) |
| Tensile strength (kgf/cm²) | 46 | 34 (−26) |
| Surface state | — | no change |

Note: Figures in parentheses are percents based on the initial, but increase or decrease of points for hardness.

TABLE 8

| Low-temperature property (German twist test) | |
|---|---|
| $T_2$ | −7° C. |
| $T_5$ | −25° C. |
| $T_{10}$ | −43° C. |
| $T_{100}$ | −52° C. |

Example 11

A composition was prepared by the same procedure as in Example 10 except that 12.5 parts of a fluorinated cyclohydrogensiloxane of the following formula (q) was used instead of the fluorinated cyclohydrogensiloxane in Example 10. A cured sheet was similarly prepared therefrom.

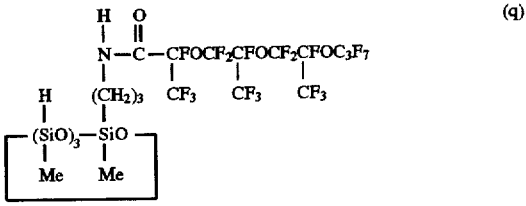  (q)

A specimen cut from the cured sheet was similarly measured for physical properties, with the results shown below.

| Hardness (JIS-A) | 43 |
| --- | --- |
| Elongation (%) | 290 |
| Tensile strength (kgf/cm$^2$) | 44 |

Example 12

A composition was prepared by the same procedure as in Example 10 except that 100 parts of a polymer of the following formula (r) having a viscosity of 42,000 centistokes at 25° C., an average molecular weight of 9,200 and an allyl content of 0.022 mol/100 g was used instead of the polymer of formula (o) and 6.1 parts of the fluorinated cyclohydrogensiloxane in Example 10 was used. A cured sheet was similarly prepared therefrom.

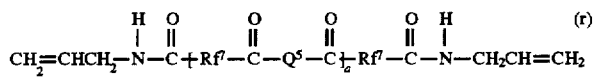

$\bar{a} = 4$

Rf$^7$: —(CF$_2$(OCF$_2$CF$_2$)$_8$(OCF$_2$)$_2$OCF$_2$—

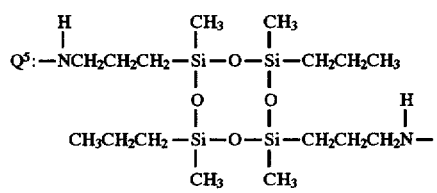

A specimen cut from the cured sheet was similarly measured for physical properties, with the results shown below.

| Hardness (JIS-A) | 35 |
| --- | --- |
| Elongation (%) | 340 |
| Tensile strength (kgf/cm$^2$) | 45 |

Example 13

A composition was prepared by the same procedure as in Example 10 except that 100 parts of a polymer of the following formula (s) having a viscosity of 178,000 centistokes at 25° C., an average molecular weight of 19,200 and an allyl content of 0.010 mol/t100 g was used instead of the polymer of formula (o) and 3.5 parts of the fluorinated cyclohydrogensiloxane in Example 10 was used. A cured sheet was similarly prepared therefrom.

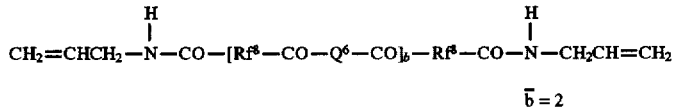

$\bar{b} = 2$

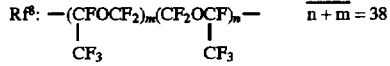   $\overline{n+m} = 38$

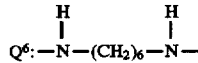

A specimen cut from the cured sheet was similarly measured for physical properties, with the results shown below.

| Hardness (JIS-A) | 42 |
| --- | --- |
| Elongation (%) | 280 |
| Tensile strength (kgf/cm$^2$) | 44 |

Example 14

A composition was prepared by the same procedure as in Example 6 except that 100 parts of a polymer of the following formula (t) having a viscosity of 3,300 centistokes at 25° C., an average molecular weight of 18,100 and an allyl content of 0.011 mol/100 g was used instead of the polymer of formula (j) and 3.1 parts of a fluorinated cyclohydrogensiloxane of the following formula (u) was used instead of the fluorinated cyclohydrogensiloxane in Example 6. A cured sheet was similarly prepared therefrom.

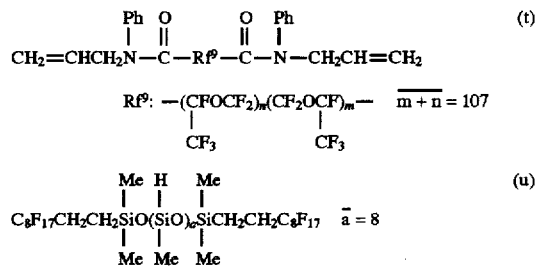

A specimen cut from the cured sheet was similarly measured for physical properties, with the results shown below.

| Hardness (JIS-A) | 46 |
| --- | --- |
| Elongation (%) | 200 |
| Tensile strength (kgf/cm$^2$) | 23 |

Japanese Patent Application Nos. 164635/1994, 164636/1994, 295789/1994, and 295790/1994 are incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. An organic fluorine compound of the following general formula:

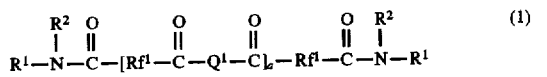

wherein $R^1$ are independently selected from substituted or unsubstituted monovalent hydrocarbon groups having an aliphatic unsaturated group, $R^2$ are independently selected from the substituted or unsubstituted monovalent hydrocarbon groups, $Q^1$ is a group represented by the following general formula (2) or (3):

wherein $R^3$ is a substituted or unsubstituted divalent hydrocarbon group which may have at least one intervening atom selected from oxygen, nitrogen and silicon atoms, $R^4$ and $R^5$ are independently selected from substituted or unsubstituted divalent hydrocarbon groups, $Rf^1$ is a divalent perfluoroalkylene or perfluoropolyether group, and letter a is an integer inclusive of 0.

2. A curable composition comprising (A) a fluorinated amide compound having at least two aliphatic unsaturated groups in a molecule and represented by the following general formula (1):

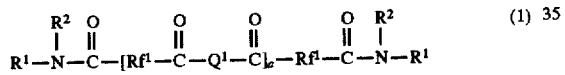

wherein $R^1$ are independently selected from substituted or unsubstituted monovalent hydrocarbon groups having an aliphatic unsaturated group, $R^2$ are independently selected from the substituted or unsubstituted monovalent hydrocarbon groups, $Q^1$ is a group represented by the following general formula (2) or (3):

wherein $R^3$ is a substituted or unsubstituted divalent hydrocarbon group which may have at least one intervening atom selected from oxygen, nitrogen and silicon atoms, $R^4$ and $R^5$ are independently selected from substituted or unsubstituted divalent hydrocarbon groups, $Rf^1$ is a divalent perfluoroalkylene or perfluoropolyether group, and letter a is an integer inclusive of 0, (B) a fluorinated organohydrogensiloxane containing at least one monovalent perfluoroalkyl ether or perfluoroalkyl group and at least two hydrosilyl groups in a molecule, and (C) a catalytic amount of a platinum group compound, component (B) being present in an amount to give 0.5 to 5 mol of the hydrosilyl group per mol of the aliphatic unsaturated group in the composition.

3. A curable composition comprising (D) a fluorinated amide compound having at least two aliphatic unsaturated groups in a molecule and represented by the following general formula (4):

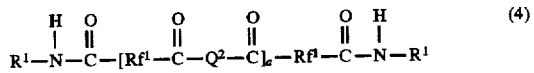

wherein $R^1$ is a substituted or unsubstituted monovalent hydrocarbon group having an aliphatic unsaturated group, $Q^2$ is a group represented by the following general formula (5):

wherein $R^3$ is a substituted or unsubstituted divalent hydrocarbon group which may have at least one intervening atom selected from oxygen, nitrogen and silicon atoms, $Rf^1$ is a divalent perfluoroalkylene or perfluoropolyether group, and letter a is an integer inclusive of 0, (E) a fluorinated organohydrogensiloxane containing in a molecule at least two hydrosilyl groups and at least one group of the following general formula (6):

wherein $Rf^2$ is a monovalent perfluoroalkyl or perfluoroalkyl ether group, $R^6$ is a divalent hydrocarbon group, and $R^7$ is a hydrogen atom or monovalent hydrocarbon group, and (C) a catalytic amount of a platinum group compound, component (E) being present in an amount to give 0.5 to 5 mol of the hydrosilyl group per mol of the aliphatic unsaturated group in the composition.

4. The compound of formula (1) of claim 1, wherein:

$R^1$ and $R^2$ are independently a monovalent hydrocarbon group of 1 to 10 carbon atoms optionally substituted with halogen atoms, $R^3$ is a divalent hydrocarbon group of 1 to 20 carbon atoms optionally substituted by halogen atoms and optionally having at least one intervening —O— group, —NR'— group where R' is hydrogen or alkyl of 1–8 carbon atoms, organosilylene group or a group containing a linear or cyclic organosiloxane, $R^4$ and $R^5$ are, independently, a divalent hydrocarbon group of 1 to 10 carbon atoms optionally substituted with halogen atoms, and a is from 0 to 10.

5. The composition of claim 2, wherein in the formula (1):

$R^1$ and $R^2$ are independently a monovalent hydrocarbon group of 1 to 10 carbon atoms optionally substituted with halogen atoms, $R^3$ is divalent hydrocarbon group of 1 to 20 carbon atoms optionally substituted by halogen atoms and optionally having at least one intervening —O— group, —NR'— group where R' is hydrogen or alkyl of 1–8 carbon atoms, organosilylene group or a group containing a linear or cyclic organosiloxane, $R^4$ and $R^5$ are, independently, a divalent hydrocarbon group of 1 to 10 carbon atoms optionally substituted with halogen atoms, and a is from 0 to 10.

6. The compound of formula (1) of claim 1, wherein $Rf^1$ is: a divalent perfluoroalkylene group of the formula $$-C_mF_m-$$

where m=1–10, or a divalent perfluoropolyether group of one of the following formulae:

$$-(CFOCF_2)_p-(CF_2)_r-(CF_2OCF)_q-$$
$$\phantom{-()}|\phantom{(CF_2)_r}|$$
$$\phantom{-()}X\phantom{(CF_2)_r}X$$

wherein X is F or $CF_3$ group, p, q and r are integers in the range: $p \geq 1$, $q \geq 1$, and $2 \leq p+q \leq 200$, $$-CF_2CF_2OCF_2-(CFOCF_2)_s-(CF_2)_r-(CF_2OCF)_t-CF_2OCF_2CF_2-$$
$$\phantom{-CF_2CF_2OCF_2-()}|\phantom{(CF_2)_r(CF_2OCF)_t}|$$
$$\phantom{-CF_2CF_2OCF_2-()}CF_3\phantom{(CF_2)_r(CF_2OCF)}CF_3$$

wherein r, s and t are integers in the range: $0 \leq r \leq 6$, $s \geq 0$, $t \geq 0$, and $2 \leq s+t \leq 200$, $$-CF-(OCFCF_2)_u-(OCF_2)_v-OCF-$$
$$\phantom{-}|\phantom{(OCFCF_2)_u}|\phantom{(OCF_2)_v}|$$
$$\phantom{-}X\phantom{(OCFCF_2)_u}X\phantom{(OCF_2)_v}X$$

wherein X is F or $CF_3$ group, u and v are integers in the range: $1 \leq u \leq 20$ and $1 \leq v \leq 20$, and $$-CF_2CF_2-(OCF_2CF_2CF_2)_w-OCF_2CF_2-$$

wherein w is an integer in the range: $1 \leq w \leq 20$.

7. The composition of claim 2, wherein in formula (1) $Rf^1$ is:

a divalent perfluoroalkylene group of the formula $$-C_mF_m-$$

where m=1–10, or a divalent perfluoropolyether group of one of the following formulae:

$$-(CFOCF_2)_p-(CF_2)_r-(CF_2OCF)_q-$$
$$\phantom{-()}|\phantom{(CF_2)_r}|$$
$$\phantom{-()}X\phantom{(CF_2)_r}X$$

wherein X is F or $CF_3$ group, p, q and r are integers in the range: $p \geq 1$, $q \geq 1$, and $2 \leq p+q \leq 200$, $$-CF_2CF_2OCF_2-(CFOCF_2)_s-(CF_2)_r-(CF_2OCF)_t-CF_2OCF_2CF_2-$$
$$\phantom{-CF_2CF_2OCF_2-()}|\phantom{(CF_2)_r(CF_2OCF)_t}|$$
$$\phantom{-CF_2CF_2OCF_2-()}CF_3\phantom{(CF_2)_r(CF_2OCF)}CF_3$$

wherein r, s and t are integers in the range: $0 \leq r \leq 6$, $s \geq 0$, $t \geq 0$, and $2 \leq s+t \leq 200$, $$-CF-(OCFCF_2)_u-(OCF_2)_v-OCF-$$
$$\phantom{-}|\phantom{(OCFCF_2)_u}|\phantom{(OCF_2)_v}|$$
$$\phantom{-}X\phantom{(OCFCF_2)_u}X\phantom{(OCF_2)_v}X$$

wherein X is F or $CF_3$ group, u and v are integers in the range: $1 \leq u \leq 20$ and $1 \leq v \leq 20$, and $$-CF_2CF_2-(OCF_2CF_2CF_2)_w-OCF_2CF_2-$$

wherein w is an integer in the range: $1 \leq w \leq 20$.

8. A compound of claim 1 having a viscosity of about 100 to about 100,000 at 25° C.

9. A composition of claim 2 wherein the compound of formula (1) has a viscosity of about 100 to about 100,000 at 25° C.

10. An elastomer obtained by curing of the composition of claim 2.

11. The compound of claim 1, wherein $R^1$ is an alkenyl group of 2–8 carbon atoms.

12. The composition of claim 1, wherein in the fluorinated organohydrogensiloxane, (B), at least one perfluoroalkyl ether or pedluoroalkyl is of one of the following formulae:

$$C_mF_{2m+1}-$$

wherein m is an integer of 1 to 10, and $$F-(CFCF_2O)_n-CF-$$
$$\phantom{F-()}|\phantom{(CFCF_2O)_n}|$$
$$\phantom{F-()}CF_3\phantom{(CFCF_2O)_n}CF_3$$

wherein n is an integer of 1 to 5.

13. The composition of claim 2, wherein component (B) is provided in an a mount of 0.1 to 50 parts by weight per 100 parts by weight of component (A).

14. The composition of claim 3, wherein:

$R^1$ is a monovalent aliphatic unsaturated hydrocarbon group of 2 to 10 carbon atoms optionally substituted with halogen atoms, $R^3$ is a divalent hydrocarbon group of 1 to 20 carbon atoms optionally substituted by halogen atoms and optionally having at least one intervening —O— group, —NR'— group where R' is hydrogen or alkyl of 1–8 carbon atoms, organosilylene group or a group containing a linear or cyclic organosiloxane, and a is from 0 to 10.

15. The composition of claim 3, wherein $Rf^1$ is:

a divalent perfluoroalkylene group of the formula $$-C_mF_m-$$

where m=1–10, or a divalent perfluoropolyether group of one of the following formulae:

$$-(CFOCF_2)_p-(CF_2)_r-(CF_2OCF)_q-$$
$$\phantom{-()}|\phantom{(CF_2)_r}|$$
$$\phantom{-()}X\phantom{(CF_2)_r}X$$

wherein X is F or $CF_3$ group, p, q and r are integers in the range: $p \geq 1$, $q \geq 1$, and $2 \leq p+q \leq 200$,

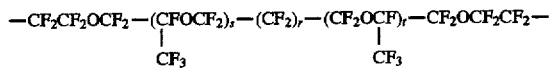

wherein r, s and t are integers in the range: $0 \leq r \leq 6$, $s \geq 0$, $t \geq 0$, and $2 \leq s+t \leq 200$,

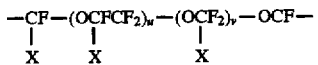

wherein X is F or $CF_3$ group, u and v are integers in the range: $1 \leq u \leq 20$ and $1 \leq v \leq 20$, and

wherein w is an integer in the range: $1 \leq w \leq 20$.

16. The composition of claim 3, wherein in formula (6) $Rf^2$ is a perfluoroalkyl ether or perfluoroalkyl of one of the following formulae:

wherein m is an integer of 1 to 10,

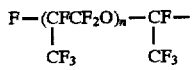

wherein n is an integer of 1 to 5;

$R^6$ is a divalent hydrocarbon group of 1–8 carbon atoms and $R^7$ is hydrogen or a monovalent hydrocarbon group of 1–8 carbon atoms optionally substituted by halogen atoms.

17. The composition of claim 3, wherein the fluorinated organohydrogensiloxane, (E), has a monovalent hydrocarbon substituent of 1–10 carbon atoms free of an aliphatic unsaturated bond attached to a silicon atom.

18. An elastomer obtained by curing the composition of claim 3.

* * * * *